United States Patent
Yang et al.

(10) Patent No.: US 10,919,024 B2
(45) Date of Patent: *Feb. 16, 2021

(54) RHENIUM CATALYSTS FOR GLYCERIN TO ALLYL ALCOHOL CONVERSION

(71) Applicant: Lyondell Chemical Technology, L.P., Houston, TX (US)

(72) Inventors: Xueyong Yang, Bellaire, TX (US); Daniel F. White, Houston, TX (US); Beaven S. Mandimutsira, Sugar Land, TX (US)

(73) Assignee: Lyondell Chemical Technology, L.P., Houston, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 16/284,804

(22) Filed: Feb. 25, 2019

(65) Prior Publication Data

US 2019/0262801 A1 Aug. 29, 2019

Related U.S. Application Data

(60) Provisional application No. 62/635,364, filed on Feb. 26, 2018, provisional application No. 62/635,339, filed on Feb. 26, 2018.

(51) Int. Cl.

| | | |
|---|---|---|
| *C07C 29/60* | (2006.01) | |
| *C07C 45/50* | (2006.01) | |
| *B01J 23/00* | (2006.01) | |
| *B01J 23/36* | (2006.01) | |
| *B01J 31/22* | (2006.01) | |
| *C07C 29/141* | (2006.01) | |
| *C07C 31/20* | (2006.01) | |
| *B01J 31/40* | (2006.01) | |
| *C07C 29/143* | (2006.01) | |
| *C07C 33/03* | (2006.01) | |
| *C07C 47/19* | (2006.01) | |

(52) U.S. Cl.
CPC .......... *B01J 23/36* (2013.01); *B01J 31/2208* (2013.01); *B01J 31/4046* (2013.01); *C07C 29/141* (2013.01); *C07C 29/143* (2013.01); *C07C 29/60* (2013.01); *C07C 31/207* (2013.01); *C07C 45/50* (2013.01); *B01J 2231/321* (2013.01); *B01J 2531/74* (2013.01); *B01J 2531/822* (2013.01); *C07C 33/03* (2013.01); *C07C 47/19* (2013.01)

(58) Field of Classification Search
CPC ....... C07C 29/60; C07C 29/141; C07C 45/50; B01J 23/36; B01J 31/2208
See application file for complete search history.

(56) References Cited

U.S. PATENT DOCUMENTS

| | | |
|---|---|---|
| 2010/0292514 A1 | 11/2010 | White |
| 2014/0005440 A1 | 1/2014 | Mandimutsira et al. |
| 2017/0121262 A1 | 5/2017 | White et al. |
| 2018/0207618 A1 | 7/2018 | Kon et al. |

FOREIGN PATENT DOCUMENTS

| | | |
|---|---|---|
| EP | 3124462 A1 | 2/2017 |
| WO | 2013181255 A1 | 12/2013 |

OTHER PUBLICATIONS

The extended European Search Report for EP19157899.6 dated Apr. 17, 2019.

*Primary Examiner* — Sikarl A Witherspoon

(57) ABSTRACT

A catalyst system for the conversion of glycerin to allyl alcohol, the catalyst system comprising: a rhenium compound selected from rhenium dioxide, rhenium trioxide, and a combination thereof. A method of producing allyl alcohol from glycerin via the catalyst system, the method comprising exposing glycerin to a temperature of greater than 140° C. in the presence of a catalyst comprising rhenium trioxide, rhenium dioxide, or a combination thereof to produce a product comprising allyl alcohol.

20 Claims, 2 Drawing Sheets

RHENIUM CATALYSTS FOR GLYCERIN TO ALLYL ALCOHOL CONVERSION

CROSS-REFERENCE TO RELATED APPLICATIONS

This application claims the benefit of priority to U.S. Provisional Patent Application Nos. 62/635,364 and 62/635,339, each filed on Feb. 26, 2018, which are incorporated herein by reference in their entirety.

TECHNICAL FIELD

This disclosure relates to catalysts for the production of allyl alcohol from glycerin. More specifically, this disclosure relates to rhenium catalysts for the production of allyl alcohol from glycerin. Still more specifically, this disclosure relates to the production of allyl alcohol from glycerin in the presence of a catalyst comprising rhenium dioxide and/or rhenium trioxide.

BACKGROUND

Allyl alcohol has been utilized to prepare polymer resins, medical products, and fine chemical products. For example, allyl alcohol is used commercially for the manufacture of 1,4-butanediol (see, for example, U.S. Pat. No. 4,215,077). It is also utilized as a hydroxyl functional monomer in the polymer industry (see, for example, U.S. Pat. No. 5,444,141).

Generally, allyl alcohol is derived from propylene obtained by petrochemical processes. Allyl alcohol can be produced by the isomerization of propylene oxide, as described, for example, in U.S. Pat. No. 3,274,121 (slurry phase process) and U.S. Pat. No. 3,044,850 (gas-phase process). Alternatively, allyl alcohol can be made from glycerin.

The conversion of glycerin to allyl alcohol (AA) has been reported, for example, by Shiramizu and Toste 2012 (Angew. Chem. Int. Ed. 2012, Vol. 51, pp. 8082-8086); Arceo, Marsden, Bergman, and Ellman 2009 (Chemical Communications, 2009, 23, 3357); Yi, Liu, and Abu-Omar 2012 (ChemSusChem, 2012, 5, 1401). Preparation of allyl alcohol from glycerin based on a two-step reaction mechanism, including a first step for dehydration of glycerin into acrolein and a second step for hydrogenation of acrolein into allyl alcohol, direct preparation of allyl alcohol from glycerin not through acrolein, as well as preparation of allyl alcohol from glycerin without the use of a catalyst have been described. Challenges with various reported preparation methods of allyl alcohol include the need for an expensive (e.g., methyltrioxorhenium) catalyst, high levels of impurities (e.g., byproducts, such as octene), and/or low allyl alcohol yield.

For example, Toste, et al. reported on the use of methyltrioxorhenium (MTO) in a reaction in which an excess (10 equivalents or more) of a secondary alcohol such as 3-octanol is utilized as the reductant as well as solvent, with reactions being carried out in a closed vessel at temperatures above 170° C. In addition to 3-octanone resulting from oxidative dehydrogenation reaction, byproduct octene isomers are formed as the result of dehydration reactions. It has been reported that, when employing MTO as catalyst and 3-octanol as solvent, glycerin can be converted to AA with a selectivity of 90%. However, for each mole of AA produced, 1.0 mole of 3-octanol was also being converted into octene isomers. The formation of a high level of octene isomers increases the cost of making allyl alcohol using an MTO/3-octanol catalyst system.

Arceo, Marsden, Bergman, Ellman reported on formic-acid mediated conversion of glycerin to allyl alcohol, with a reported 84% allyl alcohol yield via the formic acid treatment. The consumption of the formic acid increases the cost of making allyl alcohol using the formic-acid mediated process.

Accordingly, a need exists for improved catalysts and methods for the production of allyl alcohol from glycerin.

SUMMARY

Herein disclosed is a catalyst system for the conversion of glycerin to allyl alcohol, the catalyst system comprising: a rhenium compound selected from rhenium dioxide, rhenium trioxide, and a combination thereof.

Also disclosed herein is a method comprising: exposing glycerin to a temperature of greater than 140° C. in the presence of a catalyst comprising rhenium trioxide, rhenium dioxide, or a combination thereof to produce a product comprising allyl alcohol.

While multiple embodiments are disclosed, still other embodiments will become apparent to those skilled in the art from the following detailed description. As will be apparent, certain embodiments, as disclosed herein, are capable of modifications in various aspects without departing from the spirit and scope of the claims as presented herein. Accordingly, the detailed description hereinbelow is to be regarded as illustrative in nature and not restrictive.

BRIEF DESCRIPTION OF THE DRAWING

The following figure illustrates an embodiment of the subject matter disclosed herein. The claimed subject matter may be understood by reference to the following description taken in conjunction with the accompanying figure, in which:

DETAILED DESCRIPTION

Overview

Figure 1:
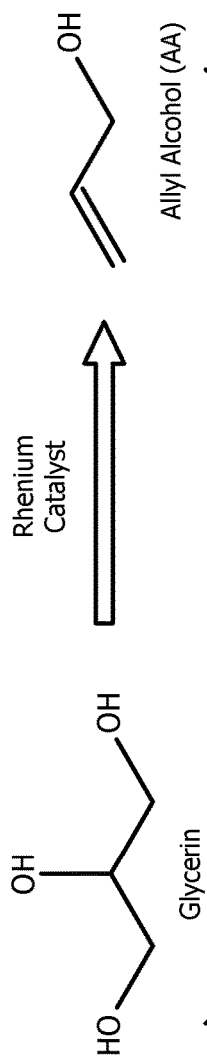
FIG. 1 is a schematic of the conversion of glycerin to allyl alcohol (AA) in the presence of the herein-disclosed rhenium catalyst, according to embodiments of this disclosure.

This disclosure relates to catalysts for the conversion of glycerin to allyl alcohol, and methods for producing allyl alcohol thereby. The herein-disclosed catalyst comprises rhenium dioxide (also referred to as rhenium (IV) oxide or $ReO_2$) and/or rhenium trioxide (also referred to as rhenium (VI) oxide or $ReO_3$), and is operable to catalyze the conversion of glycerin to allyl alcohol, as depicted in FIG. 1.

Production of Allyl Alcohol from Glycerin

According to this disclosure, allyl alcohol can be produced by subjecting glycerin to conversion conditions in the presence of the herein disclosed catalyst comprising rhenium trioxide, rhenium dioxide, or a combination thereof to produce a product comprising allyl alcohol. According to this disclosure, the glycerin may be produced or derived from any suitable source, including bio-glycerin derived from bio-fuel (e.g., bio-diesel) production and/or non-bio-glycerin derived from conventional petrochemical processes.

In embodiments, the herein-disclosed catalyst comprising rhenium dioxide and/or rhenium trioxide is present in the range of from 0.5 to 10 mole percent, from 2.5 to 7.5 mole percent, from 3 to 5 mole percent, from 4 to 5 mole percent, or from 4.5 to 5 mole percent of glycerin. In embodiments, the herein-disclosed catalyst comprising rhenium dioxide and/or rhenium trioxide is present at a level of less than or equal to 2, 3, 4, or 5 mole percent.

Glycerin, represented by the chemical formula $HOCH_2(CHOH)CH_2OH$, is also referred to as trihydroxypropane or glycerol. Although the purity of the glycerin converted to allyl alcohol via the herein-disclosed catalyst and method does not limit the scope of this disclosure, it can be 80 wt. % or higher, 90 wt. % or higher, or 95 wt. % or higher, in embodiments, in order to reduce the production of reaction byproducts. In embodiments, the glycerin is obtained as a byproduct from the synthesis of bio-diesel via transesterification of vegetable oil and alcohol. Such glycerin may be referred to as bio-glycerin or crude glycerin, and the produced allyl alcohol may thus be considered 'bio-allyl alcohol'. As used herein, 'bio-glycerol', 'bio-glycerin', 'crude glycerin', and 'crude glycerol' refer to glycerin obtained as a byproduct of bio-diesel production, and 'bio-allyl alcohol' refers to allyl alcohol derived from bio-glycerin. In embodiments, the glycerin converted to allyl alcohol via the herein disclosed rhenium catalyst and method comprises bio-glycerin, and the product comprises bio-allyl alcohol; in embodiments, the glycerin converted to allyl alcohol via the herein disclosed rhenium catalyst and method comprises non-bio-glycerin, and the product comprises non-bio-allyl alcohol; in embodiments, the glycerin converted to allyl alcohol via the herein disclosed rhenium catalyst and method comprises bio- and non-bioglycerin, and the product comprises bio-allyl alcohol and non-bio-allyl alcohol. In embodiments, at least 20, 30, 40, 50, 60, 70, 80, or 90 mole percent of the glycerin converted to allyl alcohol according to this disclosure comprises bio-glycerin. In embodiments, at least 20, 30, 40, 50, 60, 70, 80, or 90 mole percent of the glycerin converted to allyl alcohol according to this disclosure comprises non-bio-glycerin The conversion of glycerin to allyl alcohol via this disclosure can be a liquid phase reaction, and conversion conditions can comprise a reaction temperature of greater than 140° C., 150° C., 160° C., 170° C., 180° C., 190° C., or 200° C. Reaction can be effected under ambient pressure, and the reaction temperature can be increased to the operating temperature within 30 minutes in the presence of the herein-disclosed $ReO_2$ and/or $ReO_3$ catalyst.

The conversion may be effected with or without a solvent. In embodiments, the glycerin is exposed to the reaction temperature in the presence of a solvent. In embodiments, a catalyst system comprises $ReO_3$ and a solvent; in embodiments, a catalyst system comprises $ReO_2$ and a solvent; in embodiments, a catalyst system comprises $ReO_2$ and/or $ReO_3$, and a solvent. In embodiments, the solvent comprises a secondary alcohol. In embodiments, the solvent comprises 3-octanol. In embodiments comprising a solvent, an initial molar ratio of the solvent to glycerin can be in the range of from 30:1 to 1:1, from 20:1 to 1:1, from 15:1 to 1:1, from 5:1 to 1:1, from 1:1 to 1:1, or less than or equal to 15:1 to 1:1, 10:1 to 1:1, or 6:1 to 1:1.

An allyl alcohol (AA) selectivity can be defined as:

$$\text{AA Selectivity} = (([AA]_{produced})/([Glycerin]_{feed} - [Glycerin]_{unreacted})) \times 100\%, \quad (1)$$

wherein $(([AA]_{produced}$ is the molar amount of produced allyl alcohol, $[Glycerin]_{feed}$ is the molar amount of glycerin in the glycerin feed to the reaction, and $-[Glycerin]_{unreacted}$ is the molar amount of unreacted glycerin in the reaction product. The catalyst and method of this disclosure may provide for a selectivity to allyl alcohol that is, in embodiments, greater than or equal to 50%, 60%, 70%, 80%, or 90%.

A glycerin conversion can be defined as:

$$\text{Glycerin Conversion} = (([Glycerin]_{feed} - [Glycerin]_{unreacted})/([Glycerin]_{feed})) \times 100\%, \quad (2)$$

wherein $[Glycerin]_{feed}$ is the molar amount of glycerin in the feed to the reaction, and $[Glycerin]_{unreacted}$ is the molar amount of unreacted glycerin in the reaction product. The catalyst and method of this disclosure may provide for a glycerin conversion that is, in embodiments, greater than or equal to 50, 60, 70, 75, or 80 mole percent, or in the range of from 50 to 100 mole percent, from 60 to 100 mole percent, from 70 to 100 mole percent, from 70 to 90 mole percent, or from 80 to 90 mole percent.

The yield of allyl alcohol (defined by the glycerin conversion multiplied by the AA selectivity) provided by the catalyst and method of this disclosure may, in embodiments, be greater than or equal to 60%, 70%, 80%, 85%, or 90%.

As noted above, Toste, et al. reported that the use of methyltrioxorhenium (MTO) in a reaction in which an excess of a secondary alcohol such as 3-octanol is utilized as solvent, resulted in the production of 3-octanone resulting from oxidative dehydrogenation reaction, along with byproduct octene isomers formed as the result of dehydration reactions. For each mole of allyl alcohol produced, one mole of 3-octanol was converted into undesirable octene isomers. The formation of the octene isomers increases the cost of making allyl alcohol using an MTO/3-octanol catalyst system, due to removal of these octene isomers from the product allyl alcohol (or further downstream).

The herein-disclosed catalyst and method may, in embodiments employing 3-octanol as solvent, provide for a product comprising allyl alcohol that further comprises a reduced molar amount of octene isomers relative to the same method employing a methyltrioxorhenium (MTO) catalyst. For example, in embodiments, the product comprising allyl alcohol comprises less than 1.0, 0.9, 0.8, 0.7, 0.6, 0.5, 0.4, 0.3, or 0.2, 0.15, 0.11, or 0.10 mole of octene isomers per mole of allyl alcohol produced.

When employing 3-octanol as solvent, the product comprising allyl alcohol can further comprise 3-octanone as a byproduct. In such embodiments, a molar ratio of 3-octanone byproduct to allyl alcohol in the product comprising allyl alcohol can be less than or equal to 1.6, 1.5, 1.4, 1.3, 1.2, 1.1, or 1.0. In embodiments, 3-octanone is separated from the product comprising allyl alcohol. At least a portion of the separated 3-octanone can be hydrogenated to provide 3-octanol, which may be recycled for use as solvent/reductant. As 3-octanone can be readily converted back to 3-octanol for recycle and/or reuse, production of 3-octanone may be more desirable than production of octene isomers, which may be separated from the product comprising allyl alcohol, but utilizable primarily for fuel.

The method of producing allyl alcohol according to this disclosure may be carried out using any operable vessel(s) or reactor(s). For example, any one or more selected from batch reactors, continuous stirred tank reactors, and plug flow reactors, which are used by those of skill in the art, may be employed, and the kind and combination thereof are not limited herein.

Production of BDO (and/or MPD) from Allyl Alcohol

Figure 2:
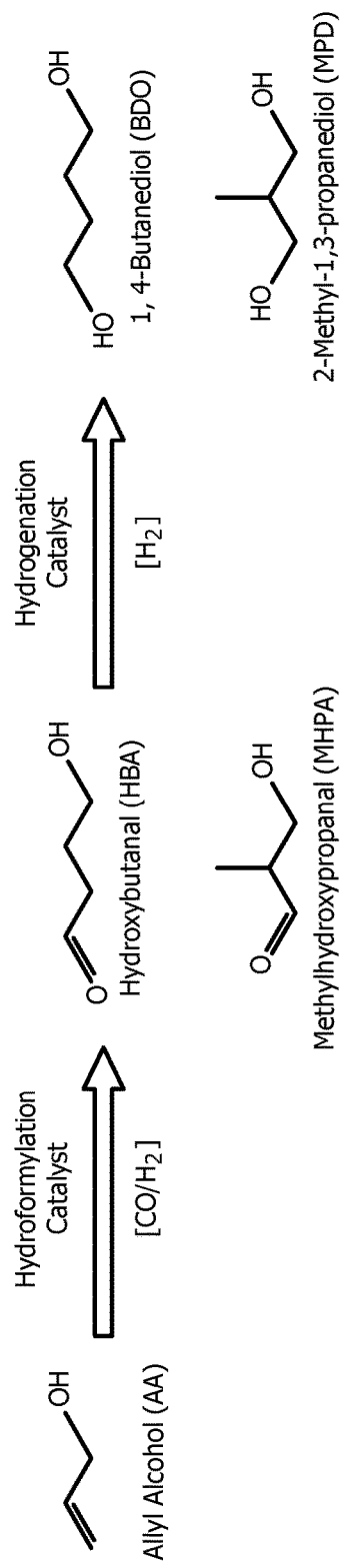
FIG. 2 is a schematic of the conversion of allyl alcohol (AA) to 1,4-butanediol (BDO) according to embodiments of this disclosure.

The allyl alcohol in the product comprising allyl alcohol may subsequently be utilized for the production of 1,4-butanediol (BDO), which occurs via the chemical pathway depicted in FIG. 2. As indicated in FIG. 2, in the hydroformylation reaction, allyl alcohol (AA) is reacted with a CO/H2 gas mixture (also referred to herein as 'synthesis gas' or 'syngas') in the presence of a hydroformylation catalyst to form 4-hydroxybutyraldehyde (HBA; also known as hydroxybutanal). The HBA may then be separated from the catalyst, e.g., by water extraction, and hydrogenated to form 1,4-butanediol (BDO). One disadvantage of the hydroformylation process is that other co-products or byproducts are also formed in addition to the desired HBA linear product. The hydroformylation of allyl alcohol typically produces some 3-hydroxy-2-methylpropionaldehyde (HMPA; also known as methylhydroxypropanal (MHPA)), which is a branched co-product, and C3 byproducts, such as, without limitation, n-propanol (NPA, n-Pr) and propionaldehyde (propanal; PA). Although HMPA may be hydrogenated to produce 1,3-methyl propanediol (MPD), which is a useful material, the MPD co-product reduces the yield of BDO. Formation of the byproducts effectively represents another yield loss in the process which can adversely affect the process economics.

Hydroformylation of Allyl Alcohol to HBA (and HMPA)

In embodiments, the product comprising allyl alcohol produced via the herein-disclosed rhenium catalyst and method is subjected to hydroformylation by contact with a hydroformylation catalyst. Hydroformylation methods and catalyst are described, for example, in U.S. Pat. Nos. 4,064,145; 4,215,077; 4,238,419; 4,567,305; 4,678,857; 5,290,743; 4,678,857; 7,294,602; 7,271,295; 7,279,606; 7,612,241, 7,655,821; 7,790,932; 8,791,305; and 8,779,211, the disclosure of each of which is hereby incorporated herein by reference in its entirety for purposes not contrary to this disclosure.

As noted above, various catalyst systems have been employed for the hydroformylation reaction. Some such hydroformylation catalysts and processes employ a rhodium complex together with a phosphine ligand. In embodiments, the process of this disclosure comprises hydroformylating allyl alcohol in the presence of a solvent and a hydroformylation catalyst system. In embodiments, the hydroformylation catalyst system comprises a rhodium complex and a phosphine ligand. Such phosphine ligands include trisubstituted phosphines such as triphenyl phosphine. In embodiments, the phosphine ligand can comprise one or more selected from diphosphine ligands, monophosphines, and combinations thereof. In embodiments, at least a portion of the allyl alcohol produced from glycerin (e.g., bio-glycerin and/or non-bio-glycerin) via the herein disclosed rhenium catalyst is hydroformylated via a hydroformylation catalyst as disclosed in U.S. Pat. Nos. 7,294,602; 7,271,295; 7,279,606; 7,612,241, 7,655,821; 7,790,932; and/or 8,779,211, In embodiments, the hydroformylation catalyst system comprises a rhodium complex and a diphosphine ligand, such as trans-1,2-bis(bis(3,5-di-n-alkylphenyl) phosphinomethyl)cyclobutane, as described, for example, in U.S. Pat. Nos. 7,294,602 and 7,279,606. In embodiments, the disphosphine ligand comprises trans-1,2-bis(bis(3,5-dimethylphenyl) phosphinomethyl) cyclobutane (also known as trans-1,2-bis[di(3,5-dimethylphenyl) phosphinomethyl] cyclobutane). Trans-1,2-bis(bis(3,5-di-n-alkyl-phenyl)phosphinomethyl) cyclobutane has the chemical structure:

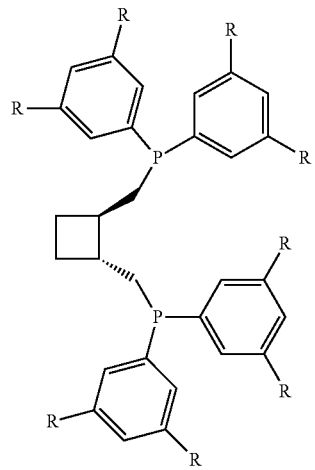

wherein R is an n-alkyl group. In embodiments, R is methyl, ethyl, or propyl. In embodiments, the disphosphine ligand can be trans-1,2-bis(bis(3,5-dimethylphenyl)phosphinomethyl)cyclobutane or trans-1,2-bis(bis(3, 5-diethyl-phenyl) phosphinomethyl)cyclobutane. The trans-1,2-bis(bis(3,5-di-n-alkylphenyl) phosphinomethyl) cyclobutane may be prepared by any possible method. For instance, it may be prepared by the reaction of trans-1,2-cyclobutanedimethanol, bis(toluenesulfonate) with lithium di(3,5-di-n-alkylphenyl)phosphine. The ligands and catalyst compositions described herein are commercially available or may be made according to the methods, procedures and processes described in Smith, M., & March, J. (2007). *Marchs Advanced organic chemistry: Reactions, mechanisms, and structure*. Hoboken, N.J.: Wiley-Interscience; Regalbuto, J. R. (2007) *Handbook of catalyst preparation*. Boca Raton: Taylor & Francis; and Kamer, P. C., (2012) *Phosphorus(III) Ligands in Homogeneous Catalysis: Design and Synthesis*. Wiley.

In embodiments, the hydroformylation catalyst system further comprises a rhodium complex. Such rhodium complexes contain rhodium attached to ligand groups. In embodiments, the rhodium complex is soluble in the solvent. There are no particular restrictions regarding the choice of ligands attached to the rhodium complex. For example, such ligands include hydrides, carbonyl, substituted and unsubstituted cyclopentadienyls, 2,4-alkanedionates, trialkyl or triaryl phosphines, diphosphines, and mixtures thereof. In embodiments, the ligands attached to the rhodium complex are selected from carbonyl, acetylacetonate (2,4-pentanedionate), triphenylphosphine, and mixtures thereof. Examples of rhodium complexes include, without limitation, (acetylacetonato)dicarbonyl rhodium(I) (also known as dicarbonyl-acetylacetonato-rhodium(I), dicarbonylrhodium (I) 2,4-pentanedionate, $Rh(CO)_2(acac)$, and rhodium(I) dicarbonyl acetylacetonate) and tris(triphenylphosphine) rhodium carbonyl hydride.

The rhodium complex can be pre-associated with the phosphine (e.g., trans-1,2-bis(bis(3, 5-di-n-alkylphenyl) phosphinomethyl)cyclobutane) prior to use in the hydroformylation reaction such that the [bis(bis(3,5-di-n-alkylphenyl)-phosphinomethyl)cyclobutane] ligand forms part of the rhodium complex, or it can be added separately. However, in embodiments, the rhodium complex is added separately from the phosphine ligand (e.g., the trans-1,2-bis (bis(3,5-di-n-alkylphenyl)phosphinomethyl)cyclobutane).

In embodiments, the molar ratio of the phosphine ligand:

rhodium complex (e.g., the trans-1,2-bis(bis(3,5-di-n-alkylphenyl)-phosphinomethyl) cyclobutane:rhodium complex) can be in the range of 0.5:1 to 5:1.

In embodiments, the hydroformylation catalyst system comprises a rhodium complex and one or more diphosphine ligands, the rhodium complex comprises $Rh(CO)_2(acac)$, and the molar ratio of $Rh(CO)_2(acac)$ to the diphosphine ligands is in the range of from 0.1:1 to 1:5, from 0.9:1.5 to 1:3, or from 1:1.9 to 1:2.1.

In embodiments, the hydroformylation catalyst system may additionally comprise an auxiliary ligand, such that the hydroformylation is further performed in the presence of the auxiliary ligand which is added to the catalyst solution. In embodiments, the auxiliary ligand comprises a monophosphine.

In embodiments, the monophosphine compound is in addition to any phosphine ligand that may be associated with the rhodium complex. In embodiments, the monophosphine compound is a trisubstituted phosphine that is represented by the formula:

$$(R^1)_3P,$$

wherein $R^1$ is an alkyl or aryl group. Aliphatic $R^1$ groups include methyl, ethyl, n-butyl, sec-butyl, octyl, and/or decyl. Aromatic $R^1$ groups include phenyl, tolyl, and/or naphthyl. The $R^1$ groups may be the same or are different. In embodiments, the monophosphine is a trisubstituted aryl phosphine. In embodiments, the monophosphine is triphenylphosphine or tritolylphosphine. In embodiments, the monophosphine is triphenyl phosphine.

In embodiments, the hydroformylation catalyst system comprises a diphosphine ligand and a monophosphine, and the monophosphine is present such that a ratio of the diphosphine to the monophosphine is in the range of from 1:1 to 1:3, from 1:1.2 to 1:2, or from 1.4 to 1.6.

Hydroformylation may be performed in the presence of a hydroformylation reaction solvent. Typical solvents are those that are capable of solubilizing the rhodium complex and are not reactive to the hydroxyaldehydes that are produced in the hydroformylation step. Solvents may include an organic solvent having very low or minimal solubility in water. In embodiments, the hydroformylation reaction solvent is selected from C5-C20 aliphatic hydrocarbons, C6-C20 aromatic hydrocarbons, alcohols, ethers, or mixtures thereof. Without limitation, in embodiments, the hydroformylation reaction solvent is selected from toluene, cyclohexane, methyl t-butyl ether, xylenes or mixtures thereof. In embodiments, the hydroformylation reaction solvent is dry degassed toluene.

Typical reaction conditions for the hydroformylation step are mild to favor the formation of the linear (1') 4-hydroxybutyraldehyde (HBA) rather than branched ('b') 3-hydroxy-2-methylpropionaldehyde (HMPA) reaction product. In embodiments, hydroformylation reaction conditions comprise temperatures in the range of from 20 to 120° C., from 45 to 85° C., from 50 to 80° C., from 35° C. to 120° C., from 45° C. to 95° C., or from 50° C. to 70° C., or greater than or equal to 55° C., 60° C., or 65° C. In embodiments, hydroformylation reaction conditions comprise pressures in the range of from 20 psig to 600 psig, from 30 psig to 400 psig, from 40 psig to 300 psig, from 100 psig to 400 psig, or from 120 psig to 300 psig, or greater than or equal to 180 psig, 190 psig, or 200 psig.

The molar ratio of carbon monoxide to hydrogen (CO:H2) can be about 1:1, although the ratio can vary considerably. In embodiments, the synthesis gas comprises a molar ratio of carbon monoxide to hydrogen in the range of from 0.5:1.5 to 1.5:0.5, from 0.8:1.2 to 0.9:1.1, or from 0.95:1.05 to 0.98:1.12, or greater than or equal to 1:1.

The partial pressure of CO may be within the range of 5 to 100 psig. The partial pressure of hydrogen may be within the range of 40 to 200 psig. In embodiments, the hydroformylation reaction is conducted at these conditions until a predominance of the allyl alcohol has reacted, e.g. 60 to 99.9 mole percent, the products comprising primarily 4-hydroxybutyraldehyde (HBA) with some branched reaction products. The amount of reaction time may not be critical, however, a reaction time of from 0.5 to 4 hours may be adequate.

In embodiments, the allyl alcohol starting concentration on a hydroformylation reaction solvent to feed basis is in the range of from 5 to 40 percent by weight in the solvent; in embodiments, an allyl alcohol starting concentration on a hydroformylation reaction solvent to feed basis in the range of from 5 to 10 percent by weight may be utilized.

In embodiments, the hydroformylation of allyl alcohol is carried out such that the concentration of CO in the liquid phase ($[CO]_{liq}$) is maintained above 4 mmols/liter (0.004 M) during the hydroformylation. The value of $[CO]_{liq}$ is defined in U.S. Pat. No. 6,225,509, the teachings of which are incorporated herein by reference for purposes not contrary to this disclosure. In embodiments, the liquid phase hydrogen:carbon monoxide molar ratio is in the range of from 10:1 to 1:2, or from 5:1 to 1:2.

The conversion of allyl alcohol to hydroformylation product can be defined as:

$$\text{AA Conversion} = (([AA]_{feed} - [AA]_{unreacted})/([AA]_{feed})) \times 100\%, \quad (3)$$

wherein $[AA]_{feed}$ is the molar amount of allyl alcohol in the feed to the hydroformylation reaction, and $[AA]_{unreacted}$ is the molar amount of unreacted allyl alcohol in the hydroformylation reaction product. In embodiments, the conversion of allyl alcohol to hydroformylation product is greater than or equal to 99.0, 99.1, 99.2, 99.3, 99.4, 99.5, 99.6, 99.7, or 99.8 mole percent.

In embodiments, a molar ratio of HBA to HMPA in the hydroformylation product is greater than or equal to 10, 10.5, 11, or 11.5. In embodiments, the hydroformylation product further comprises one or more byproducts selected from C3 products, including n-propanol, propionaldehyde, and combinations thereof. In embodiments, a sum total amount of the one or more byproducts (i.e., products other than HBA and HMPA) is less than or equal to 0.5, 0.4, or 0.3 mole percent.

Hydrogenation of Hydroformylation Product

In embodiments, following the hydroformylation step, the HBA product is separated from the solvent and hydroformylation catalyst system, for example via water extraction in an extraction vessel. Any water extraction methods may be used and can be effected by any means, such as mixer-settlers, packed or trayed extraction columns, rotating disk contactors, or passed to a settling tank for resolution of the mixture into aqueous and organic phases. HBA, and any HMPA, remain soluble in the water (aqueous) phase and are separated from the solvent (organic) phase.

The HBA (and/or any HMPA) in the hydroformylation product can be hydrogenated to provide BDO (and/or MPD). Thus, in embodiments, the HBA (and any HMPA) reaction product is subjected to an additional step of hydrogenating the HBA in the presence of a hydrogenation catalyst to produce BDO. The hydrogenation may be performed via any operable method, for example, as described in U.S. Pat. No. 6,969,780 or 5,504,261, the disclosure of each of which is hereby incorporated herein in its entirety for purposes not contrary to this disclosure. As indicated in the schematic of FIG. 2, hydrogen can be added to the reaction vessel for the hydrogenation. Hydrogenation catalysts include any Group VIII metal, such as nickel, cobalt, ruthenium, platinum, and palladium, as well as copper, zinc and chromium and mixtures and alloys thereof. In embodiments, the hydrogenation catalyst is selected from nickel catalysts. In embodiments, the hydrogenation catalyst is selected from RANEY®-type nickel and fixed bed nickel catalysts.

In embodiments, the hydrogenation reaction is carried out at a temperature in the range of from 60 to 200° C., from 80 to 140° C., or from 95 to 105° C. In embodiments, the hydrogenation is carried out at a pressure in the range of from 200 to 1000 psig, from 300 to 1000 psig, or from 700 to 900 psig. In embodiments, the hydrogenation is effected for a hydrogenation reaction time in the range of from 1 to 10 hours. During the hydrogenation reaction, BDO and MPD are formed. In embodiments, a high ratio of linear to branched products (i.e., BDO to MPD) is achieved, along with a low amount of any other co-product/byproducts (e.g., n-propanol). In embodiments, the molar ratio of BDO to MPD in the hydrogenation product is greater than or equal to 10, 10.5, 11, or 11.5. In embodiments, the hydrogenation further comprises one or more byproducts selected from C3 products, including n-propanol. In embodiments, a sum total amount of the one or more byproducts (i.e., products other than BDO and MPD) is less than or equal to 0.5, 0.4, or 0.3 mole percent.

As noted hereinabove, in embodiments, the allyl alcohol is produced, at least in part from bio-glycerin, and is thus considered herein a 'bio-allyl alcohol'; in such embodiments, the subsequently produced BDO may be considered a 'bio-BDO'. In embodiments, at least a portion of the allyl alcohol produced via the catalyst and method of this disclosure is converted to BDO, as disclosed in U.S. Patent Application No. 62/635,339, incorporated herein by reference in its entirety for purposes not contrary to this disclosure.

Features/Potential Benefits

The herein-disclosed rhenium catalysts and methods enable the production of allyl alcohol from glycerin. In embodiments, the herein-disclosed rhenium catalysts and methods enable production of allyl alcohol from bio-glycerin. In embodiments, the herein-disclosed rhenium catalysts and methods enable the production of allyl alcohol from glycerin in the presence of a 3-octanol solvent, with a reduced amount of octene isomers in the product relative to the same method employing MTO catalyst.

The following examples merely illustrate the system and method of this disclosure. Those skilled in the art will recognize many variations that are within the spirit of this disclosure and the scope of the claims.

EXAMPLES

Example 1: ReO$_3$/3-Octanol and ReO$_2$/3-Octanol Catalyst Systems

Two catalyst systems according to this disclosure, one comprising rhenium dioxide and a second comprising rhenium trioxide, were utilized to convert glycerin to allyl alcohol via the method of this disclosure. As solvent and reductant, 3-octanol was employed. For comparison, an MTO/3-octanol catalyst system was also studied. Specifically, glycerin (obtained from SIGMA ALDRICH) was exposed to the catalyst at a temperature of 170° C. for a time period of 0.1 to 4 hours. Rhenium dioxide, rhenium trioxide, MTO, and 3-octanol were obtained from SIGMA ALDRICH.

Figure 3:
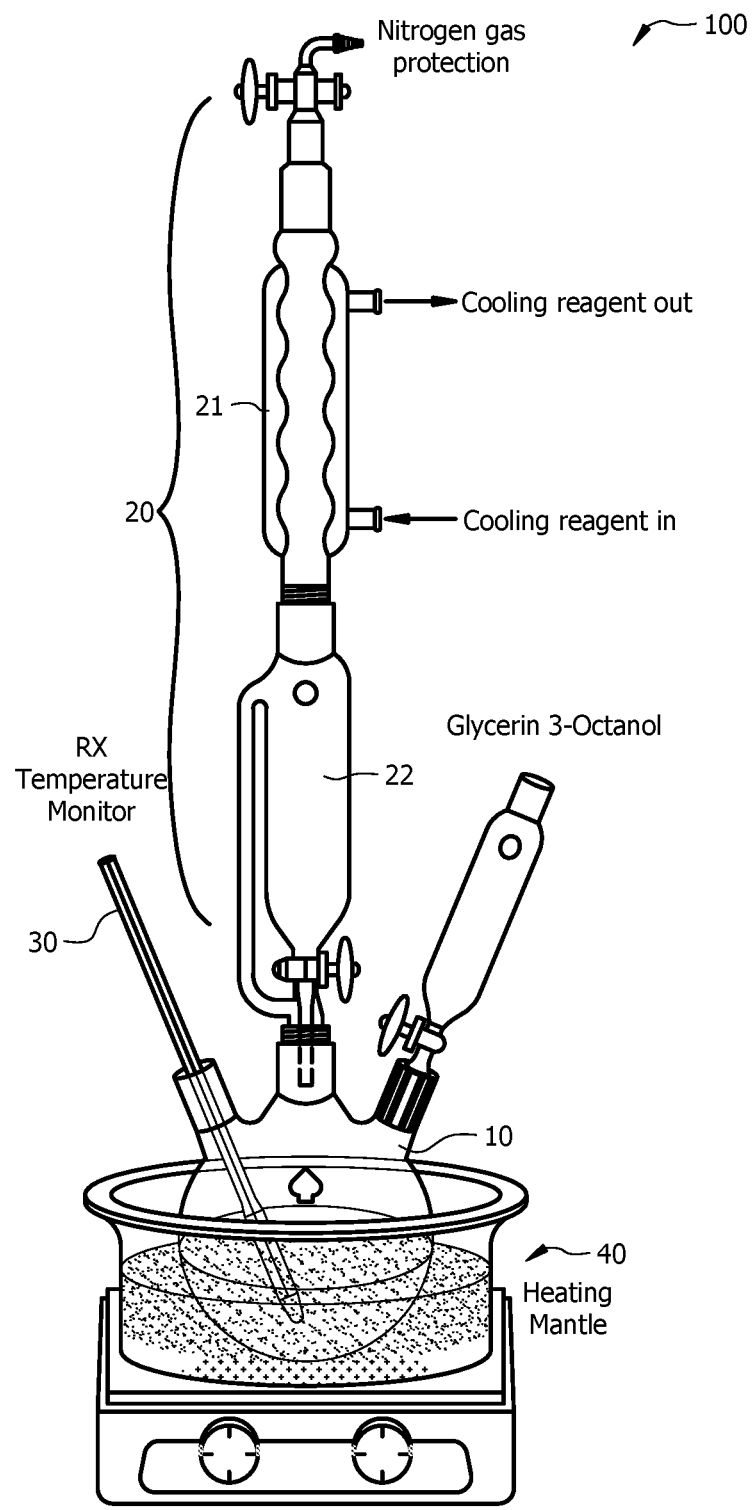
FIG. 3 is a schematic of an experimental setup 100 used in Example 1.

FIG. 3 is a schematic of an experimental setup 100 utilized in this experiment. In a 100 mL three neck round-bottom flask 10 were placed 30 mmol (2.76 g) of glycerin, 450 mmol (58.6 g) 3-octanol and 0.75 mmol MTO (or other rhenium catalysts) (0.187 g). The flask 10 was connected to a distillation set 20 (including thermocouple, distillation column 21 and collecting flask 22). The temperature in the reaction mixture was measured and controlled by an immersed thermocouple 30. The system was heated up to the operating temperature using a heating mantle 40. About 30 minutes later, a first distillation drop was collected. The reaction subsequently remained at the operating temperature for an additional 3.5 hours. Once the reaction was completed and the reaction mixture cooled to room temperature, the products were drained back to reaction mixtures for Nuclear Magnetic Resonance spectroscopy (NMR) analysis. A typical NMR sample was prepared by mixing reaction products (1.5 g), 3-hydroxyl-tetrahydrofuran (0.1 g, as internal reference for NMR quantification), and dimethyl sulfoxide-d6 (1.5 g, NMR solvent). Then a quantitative 1D 13C NMR experiment was collected to quantify the reaction mixture.

The molar ratio of 3-octanol to glycerin and the mole percent catalyst utilized for each experiment are tabulated in Table 1. The allyl alcohol selectivity calculated as per Equation (1), the molar percent glycerin conversion calculated as per Equation (2), the mole ratio of 3-octanone to allyl alcohol in the product comprising allyl alcohol, and the mole ratio of octene isomers to allyl alcohol in the product comprising allyl alcohol are also provided in Table 1.

TABLE 1

Data from Example 1
Comparison of ReO$_2$, ReO$_3$, and MTO Catalyst Systems

| Catalyst System | ReO$_2$ | ReO$_3$ | MTO |
| --- | --- | --- | --- |
| 3-Octanol/Glycerin (Molar Ratio) | 7.7 | 4.9 | 14.3 |
| Catalyst (% Molar) | 4.8 | 4.8 | 5.1 |
| Glycerin Conversion (% Molar) | 70 | 86 | 100 |
| AA Selectivity (% Molar) | 82 | 70 | 90 |
| Ratio of 3-Octanone to Produced AA (Molar Ratio) | 1.40 | 1.07 | 1.06 |
| Octene Isomers per Produced AA (Molar Ratio) | 0.11 | 0.24 | 1.09 |

The ReO$_3$ catalyst provided an improved allyl alcohol selectivity of 92% (at a solvent ratio of 15), along with reduced octene isomer formation (0.30 moles of octene isomers per mole of allyl alcohol produced). Changing the solvent ratio (i.e., the molar ratio of 3-octanol to glycerin in the feed), was also studied; by changing the solvent ratio, octene formation was reduced to 0.24 moles per mole of allyl alcohol, at a reduced allyl alcohol selectivity of 70%, as shown in Table 1. With ReO$_2$ catalyst, allyl alcohol selectivity of 80% was achieved, along with reduced octene isomer formation (0.11 moles of octene isomers per mole of allyl alcohol produced). Thus, the novel ReO$_2$/3-octanol and ReO$_3$/3-octanol catalyst systems of this disclosure unexpectedly provided for conversion of glycerin to allyl alcohol with high allyl alcohol selectivity, and reduced octene isomer byproduct formation relative to the MTO/3-octanol catalyst system.

ADDITIONAL DISCLOSURE

The particular embodiments disclosed above are illustrative only, as the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and such variations are considered within the scope and spirit of the present disclosure. Alternative embodiments that result from combining, integrating, and/or omitting features of the embodiment(s) are also within the scope of the disclosure. While compositions and methods are described in broader terms of "having", "comprising," "containing," or "including" various components or steps, the compositions and methods can also "consist essentially of" or "consist of" the various components and steps. Use of the term "optionally" with respect to any element of a claim means that the element is required, or alternatively, the element is not required, both alternatives being within the scope of the claim.

Numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an", as used in the claims, are defined herein to mean one or more than one of the element that it introduces. If there is any conflict in the usages of a word or term in this specification and one or more patent or other documents, the definitions that are consistent with this specification should be adopted.

Embodiments disclosed herein include:

A: A catalyst system for the conversion of glycerin to allyl alcohol, the catalyst system comprising: a rhenium compound selected from rhenium dioxide, rhenium trioxide, and a combination thereof.

B: A method comprising: exposing glycerin to a temperature of greater than 140° C. in the presence of a catalyst comprising rhenium trioxide, rhenium dioxide, or a combination thereof to produce a product comprising allyl alcohol.

Each of embodiments A and B may have one or more of the following additional elements:

Element 1: wherein the catalyst system further comprises 3-octanol. Element 2: wherein the glycerin is exposed to the temperature of greater than 140° C. in a solvent. Element 3: wherein the solvent comprises a secondary alcohol. Element 4: wherein the secondary alcohol comprises 3-octanol. Element 5: wherein the product comprises a reduced molar amount of octene isomers relative to the same method employing a methyltrioxorhenium (MTO) catalyst. Element 6: wherein the reduced molar amount of octene isomers comprises less than 1.0, 0.9, 0.8, 0.7, 0.6, 0.5, 0.4, 0.3, or 0.2, 0.15, or 0.12 mole of octene isomers per mole of allyl alcohol. Element 7: wherein an allyl alcohol (AA) selectivity, defined as AA Selectivity=$(([AA]_{produced})/([Glycerin]_{feed}-[Glycerin]_{unreacted}))\times 100\%$, is greater than or equal to 50%, 60%, 70%, 80%, or 90%. Element 8: wherein the product comprising allyl alcohol further comprises 3-octanone byproduct. Element 9: further comprising separating 3-octanone from the product comprising allyl alcohol, and hydrogenating at least a portion of the separated 3-octanone to provide 3-octanol. Element 10: wherein a molar ratio of 3-octanone byproduct to allyl alcohol in the product comprising allyl alcohol is less than or equal to 1.6, 1.5, 1.4, 1.3, 1.2, 1.1, or 1.0. Element 11: wherein an initial molar ratio of the solvent to glycerin is in the range of from 30 to 1, from 20 to 1, from 15 to 1, from 5 to 1, from 1 to 1, or less than or equal to 6 to 1. Element 12: wherein the catalyst is present in the range of from 0.5 to 10, from 2.5 to 7.5, from 3 to 5, from 4 to 5, or from 4.5 to 5 mole percent, or less than or equal to 3, 4, or 5 mole percent. Element 13: wherein a glycerin conversion, defined as: Glycerin Conversion= $(([Glycerin]_{feed}-[Glycerin]_{unreacted})/([Glycerin]_{feed}))\times 100\%$, is greater than or equal to 50, 60, 70, 75, or 80 mole percent, or in the range of from 50 to 100, 60 to 100, 70 to 100, 70 to 90, or 80 to 90 mole percent. Element 14: wherein the glycerin comprises bio-glycerin, and the allyl alcohol comprises bio-allyl alcohol. Element 15: wherein the glycerin comprises non-bio-glycerin, and the allyl alcohol comprises non-bio-allyl alcohol. Element 16: further comprising hydroformylating the allyl alcohol with synthesis gas to produce a hydroformylation product comprising 4-hydroxybutyraldehyde (HBA) and 3-hydroxy-2-methylpropionaldehyde (HMPA). Element 17: wherein hydroformylation is performed in dry degassed toluene, with a rhodium catalyst in the presence of phosphine ligands. Element 18: wherein the hydroformylation is performed in the presence of a catalyst solution comprising a rhodium catalyst comprising $Rh(CO)_2(acac)$ and one or more phosphine ligands. Element 19: wherein the one or more phosphine ligands comprise a diphosphine, and wherein the molar ratio of $Rh(CO)_2(acac)$ to the diphosphine ligands is from 0.1:1 to 1:5, from 0.9:1.5 to 1:3, or from 1:1.9 to 1:2.1. Element 20: wherein the diphosphine ligand comprises trans-1,2-bis[di(3,5-dimethylphenyl)phosphinomethyl]cyclobutane. Element 21: wherein the hydroformylation is further performed in the presence of an auxiliary ligand which is added to the catalyst solution. Element 22: wherein the auxiliary ligand comprises a monophosphine. Element 23: wherein the monophosphine is present such that a ratio of the diphosphine to the monophosphine is in the range of from 1:1 to 1:3, from 1:1.2 to 1:2, or from 1.4 to 1.6. Element 24: wherein the monophosphine comprises triphenylphosphine. Element 25: wherein the hydroformylation is carried out at a pressure in the range of from 20 psig to 600 psig, from 100 psig to 400 psig, or from 120 psig to 300 psig, or greater than or equal to 180 psig, 190 psig, or 200 psig, and a temperature in the range of from 35° C. to 120° C., from 45° C. to 95° C., or from 50° C. to 70° C., or greater than or equal to 55° C., 60° C., or 65° C. Element 26: wherein a conversion of allyl alcohol to hydroformylation product, defined as: AA Conversion=$(([AA]_{feed}-[AA]_{unreacted})/([AA]_{feed}))\times 100\%$, is greater than or equal to 99.0, 99.1, 99.2, 99.3, 99.4, 99.5, 99.6, 99.7, or 99.8 mole percent. Element 27: wherein a molar ratio of HBA to HMPA in the hydroformylation product is greater than or equal to 10, 10.5, 11, or 11.5. Element 28: wherein the hydroformylation product further comprises one or more byproducts selected from C3 products, including n-propanol, propionaldehyde, and combinations thereof, and wherein a sum total amount of the one or more byproducts is less than or equal to 0.5, 0.4, or 0.3 mole percent. Element 29: further comprising hydrogenating the hydroformylation product to produce a 1,4-butanediol (BDO) product comprising BDO and 1,3-methylpropanediol (MPD). Element 30: wherein the synthesis gas comprises a molar ratio of carbon monoxide to hydrogen in the range of from 0.5:1.5 to 1.5:0.5, from 0.8:1.2 to 0.9:1.1, or from 0.95:1.05 to 0.98:1.12, or greater than or equal to 1:1.

While certain embodiments have been shown and described, modifications thereof can be made by one skilled in the art without departing from the teachings of this disclosure.

Numerous other modifications, equivalents, and alternatives, will become apparent to those skilled in the art once the above disclosure is fully appreciated. It is intended that the following claims be interpreted to embrace such modifications, equivalents, and alternatives where applicable. Accordingly, the scope of protection is not limited by the description set out above but is only limited by the claims which follow, that scope including equivalents of the subject matter of the claims.

What is claimed is:

1. A method comprising:
exposing glycerin to a temperature of greater than 140° C. in the presence of a catalyst comprising rhenium trioxide, rhenium dioxide, or a combination thereof to produce a product comprising allyl alcohol and 3-octanone,
wherein the catalyst is present in the range of 0.5 to 10 mole percent.

2. The method of claim 1, wherein the glycerin is exposed to the temperature of greater than 140° C. in a solvent.

3. The method of claim 2, wherein the solvent comprises a secondary alcohol.

4. The method of claim 3, wherein the secondary alcohol comprises 3-octanol.

5. The method of claim 4, wherein the product comprises allyl alcohol and 3-octanone in a molar ratio of 3-octanone to allyl alcohol of less than 1.6.

6. The method of claim 5 further comprising separating 3-octanone from the product comprising allyl alcohol, and hydrogenating at least a portion of the separated 3-octanone to provide 3-octanol.

7. The method of claim 1, wherein the catalyst is present in the range of from 2.5 to 7.5 mole percent.

8. The method of claim 1, wherein the glycerin comprises bio-glycerin, and the allyl alcohol comprises bio-allyl alcohol.

9. The method of claim 1 further comprising hydroformylating the allyl alcohol with synthesis gas to produce a hydroformylation product comprising 4-hydroxybutyraldehyde (HBA) and 3-hydroxy-2-methylpropionaldehyde (HMPA).

10. The method of claim 9, wherein hydroformylation is performed in anhydrous toluene, with a rhodium catalyst in the presence of phosphine ligands.

11. The method of claim 9, wherein the hydroformylation is performed in the presence of a catalyst solution comprising a rhodium catalyst comprising $Rh(CO)_2(acac)$ and one or more phosphine ligands.

12. The method of claim 11, wherein the one or more phosphine ligands comprise a diphosphine, and wherein the molar ratio of $Rh(CO)_2(acac)$ to the diphosphine ligands is from 0.1:1 to 1:5.

13. The method of claim 12, wherein the auxiliary ligand comprises a monophosphine.

14. The method of claim 12, wherein the monophosphine is present such that a ratio of the diphosphine to the monophosphine is in the range of from 1:1 to 1:3.

15. The method of claim 9, wherein the hydroformylation is carried out at a pressure in the range of from 20 psig to 600 psig, and a temperature in the range of from 35° C. to 120° C.

16. The method of claim 9, wherein a molar ratio of HBA to HMPA in the hydroformylation product is greater than or equal to 10.

17. The method of claim 9 further comprising hydrogenating the hydroformylation product to produce a 1,4-butanediol (BDO) product comprising BDO and 1,3-methylpropanediol (MPD).

18. The method of claim 9, wherein the synthesis gas comprises a molar ratio of carbon monoxide to hydrogen in the range of from 0.5:1.5 to 1.5:0.5.

19. A catalyst system for the conversion of glycerin to allyl alcohol, the catalyst system comprising: a rhenium compound selected from rhenium dioxide, rhenium trioxide, and a combination thereof, wherein the catalyst is present in an amount ranging from 0.5 to 10 mole percent.

20. The catalyst system of claim 19 further comprising 3-octanol.

* * * * *